(12) United States Patent
Doty et al.

(10) Patent No.: US 7,912,539 B2
(45) Date of Patent: Mar. 22, 2011

(54) CATHETER-BASED, DUAL BALLOON PHOTOPOLYMERIZATION SYSTEM

(75) Inventors: David Doty, Forestville, CA (US);
Feridun Ozdil, Santa Rosa, CA (US);
Josiah Wilcox, Santa Rosa, CA (US);
Robret Murray, Santa Rosa, CA (US);
Prasad Kilari, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 152 days.

(21) Appl. No.: 12/363,872

(22) Filed: Feb. 2, 2009

(65) Prior Publication Data
US 2009/0171265 A1   Jul. 2, 2009

Related U.S. Application Data

(62) Division of application No. 11/166,850, filed on Jun. 23, 2005, now Pat. No. 7,515,957.

(51) Int. Cl.
*A61N 1/30* (2006.01)
*A61B 18/18* (2006.01)

(52) U.S. Cl. .................. 604/21; 604/20; 606/2

(58) Field of Classification Search ............ 604/96.01, 604/101.01, 101.03, 101.05, 20, 21; 606/2
See application file for complete search history.

(56) References Cited

U.S. PATENT DOCUMENTS

| | | | | |
|---|---|---|---|---|
| 4,198,981 | A * | 4/1980 | Sinnreich | 606/193 |
| 5,441,497 | A | 8/1995 | Narciso et al. | |
| 5,665,063 | A | 9/1997 | Roth et al. | |
| 6,030,411 | A | 2/2000 | Lawandy et al. | |
| 6,159,236 | A | 12/2000 | Biel et al. | |
| 6,569,146 | B1 * | 5/2003 | Werner et al. | 604/509 |
| 2002/0091407 | A1 * | 7/2002 | Zadno-Azizi et al. | 606/200 |
| 2003/0104073 | A1 * | 6/2003 | Johansson et al. | 424/600 |
| 2003/0163156 | A1 * | 8/2003 | Hebert et al. | 606/194 |
| 2004/0093044 | A1 | 5/2004 | Rychnovsky et al. | |

FOREIGN PATENT DOCUMENTS

EP  0448004  9/1991
WO  WO 2005/007216  1/2005

* cited by examiner

*Primary Examiner* — Nicholas D Lucchesi
*Assistant Examiner* — Victoria P Campbell

(57) ABSTRACT

A system for applying a polymer (hydrogel) to the inner surface of a vessel by photopolymerization includes a catheter having a first inflatable member and a guidewire having a second inflatable member. The catheter has an extended tip distal to the first inflatable member that includes multiple perfusion ports. A light emission coil is disposed on the extended tip with individual coil loops interspaced with the perfusion ports. In a method, the guidewire is delivered to a treatment site within a vessel. The catheter is delivered to the treatment site over the guidewire. The inflatable members are inflated to form an enclosed treatment space within the vessel. A photoinitiator is delivered to the enclosed treatment space. Excess photoinitiator is flushed from the treatment space, and a prepolymer is delivered. The prepolymer is cured by light delivered by the light emission coil.

8 Claims, 7 Drawing Sheets

US 7,912,539 B2

CATHETER-BASED, DUAL BALLOON PHOTOPOLYMERIZATION SYSTEM

RELATED APPLICATIONS

This application is a Division of and claims the benefit of U.S. patent application Ser. No. 11/166,850 filed Jun. 23, 2005 now U.S. Pat. No. 7,515,957.

TECHNICAL FIELD

This invention relates generally to biomedical systems for treating vascular conditions. More specifically, the invention relates to a catheter-based, dual balloon photopolymerization system.

BACKGROUND OF THE INVENTION

Photopolymerization, i.e., polymerization induced by light, is used to convert a liquid monomer or macromer to a polymer using visible or ultraviolet radiation. Some types of cross-linked hydrophilic polymers known as hydrogels may be formed in vivo using photopolymerization. These hydrogels exhibit good biocompatibility, making them attractive materials for use in a variety of biomedical applications.

Formation of photopolymerized hydrogels in vivo can be accomplished using bulk or interfacial photopolymerization. In bulk photopolymerization, a photoinitiator is dissolved in a hydrogel precursor (prepolymer) solution. A photoinitiator is a material that has a high absorption at a specific wavelength of light to produce radical initiating species that convert a prepolymer to a polymer. Upon exposure to an appropriate wavelength of light, the hydrogel precursor and photoinitiator solution is converted to the hydrogel state.

In interfacial photopolymerization, a photoinitiator is adsorbed onto the surface of tissues or cells. Eosin photoinitiators are commonly used because of their high affinity for tissues. A prepolymer, in this case a hydrogel precursor solution, is then delivered to the site, and the site is exposed to an appropriate light source. Polymerization occurs at the tissue interface, where the hydrogel precursor is in contact with the adsorbed photoinitiator.

Interfacial photopolymerization may be used to form thin hydrogel linings on various tissue surfaces, including the inner walls of vessels carrying bodily fluids. Dual occlusion catheters are currently used over standard guidewires to deliver photoinitiators and prepolymers to target vessels. Because a typical dual occlusion catheter requires a separate inflation lumen for each balloon, the catheter is bulky, having an undesirably large crossing profile. In addition, as currently performed, the photopolymerization procedure requires that the guidewire over which the catheter is delivered be withdrawn prior to activating the prepolymer using a light source. If left in place, the guidewire produces a shadow on the wall of the vessel, resulting in incomplete coverage of the vessel with a polymer coating. The additional step of withdrawing the guidewire adds to the time required to perform the photopolymerization procedure, posing some risk that the vessel may be damaged or other complications may occur. Complications can occur if the vessel is occluded for more than 60 seconds.

Therefore, it would be desirable to have an improved catheter-based photopolymerization system and treatment method that overcome the aforementioned and other disadvantages.

SUMMARY OF THE INVENTION

One aspect of the present invention is a system for treating a vascular condition. The system comprises a catheter, a light emission coil, a guidewire, and two inflatable members. The light emission coil is disposed on an extended tip of the catheter, coaxial with the extended tip. One inflatable member is disposed on the catheter proximal to the extended tip. The second inflatable member is disposed on a distal portion of the guidewire.

Another system for treating a vascular condition comprises catheter means for occluding a vessel proximal to the treatment site, guidewire means for occluding the vessel distal to a treatment site, means for delivering a fluid to the treatment site, and means for exposing the treatment site to light along a helical path.

Yet another system for treating a vascular condition comprises a catheter, multiple elongate light emission members, a guidewire, and two inflatable members. The light emission members are distributed about the circumference of an extended tip of the catheter. One inflatable member is disposed on the catheter proximal to the extended tip. The second inflatable member is disposed on a distal portion of the guidewire.

Another aspect of the present invention is a method of treating a vascular condition. A guidewire that includes a first expandable member is delivered to a treatment site within a vessel. A catheter that includes a second expandable member is delivered over the guidewire to the treatment site. The first and second expandable members are expanded to form an enclosed treatment space within the vessel. A fluid is delivered to the treatment space. The treatment space is exposed to light.

The aforementioned and other features and advantages of the invention will become further apparent from the following detailed description, read in conjunction with the accompanying drawings, which are not to scale. The detailed description and drawings are merely illustrative of the invention rather than limiting, the scope of the invention being defined by the appended claims and equivalents thereof.

BRIEF DESCRIPTION OF THE DRAWINGS

Like reference numbers are used throughout the drawings to refer to like elements.

DETAILED DESCRIPTION

Figure 1:
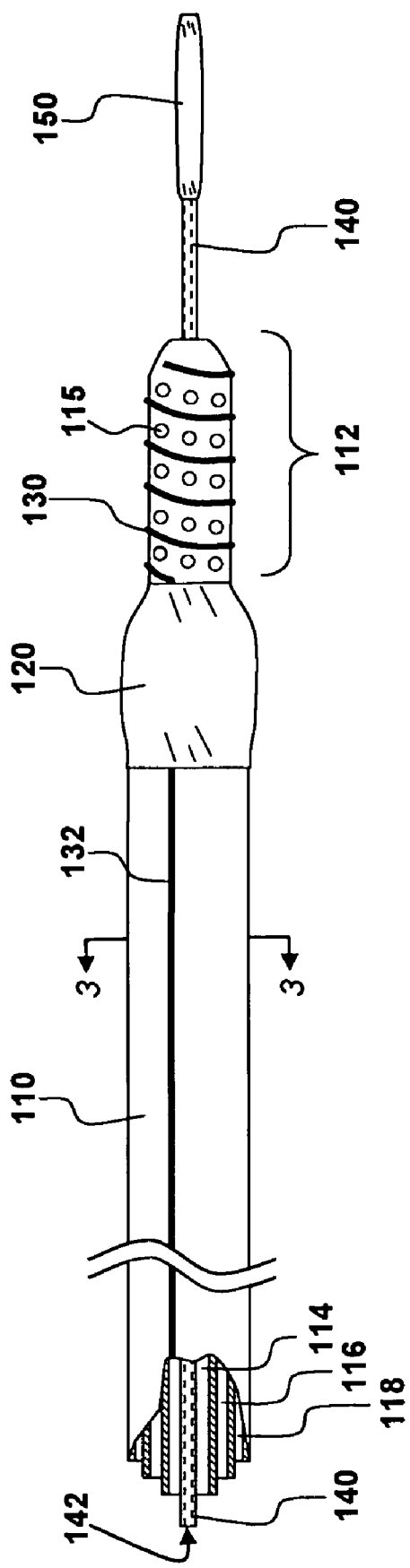
FIG. 1 is an illustration of one embodiment of a system for treating a vascular condition, in accordance with the present invention, showing the system as it would appear when partially delivered to a treatment site within a vessel.

One aspect of the present invention is a system for treating a vascular condition. The system, illustrated in FIGS. 1 and 2 at 100, comprises a catheter 110, a proximal balloon 120, a light emission coil 130, a guidewire 140, and a distal balloon 150. Catheter 110 has an extended tip 112. A proximal portion of catheter 110 is cut away to reveal a guidewire lumen 114, a fluid delivery lumen 116, and an inflation lumen 118. Multiple perfusion ports 115 are formed in extended tip 112. Guidewire 140 includes an inflation lumen 142.

Catheter 110 includes extended tip 112, which forms a distal portion of catheter 110. Multiple perfusion ports 115 are formed in extended tip 112 by, for example, drilling or laser cutting. In the present embodiment, perfusion ports 115 are substantially circular openings having a diameter of about 0.010 inch. The ports are distributed about the circumference of extended tip 112, with the number of openings chosen depending on the length of extended tip 112. As just one example, 40 to 60 perfusion ports may be formed in an extended tip having a length of 8 millimeters. As will be apparent to one skilled in the art, the number, size, and shape of the perfusion ports may be varied as needed. For example, in an alternative embodiment, the perfusion ports may be vertical slots, horizontal slits, and the like.

In the present embodiment, system 100 is used to apply a polymer coating to the inner surface of a blood or other vessel by interfacial photopolymerization using a photoinitiator. To prevent formation of a polymer coating on the exterior of extended tip 112, the tip may comprise a material that does not absorb or otherwise retain the photoinitiator.

Figure 3:
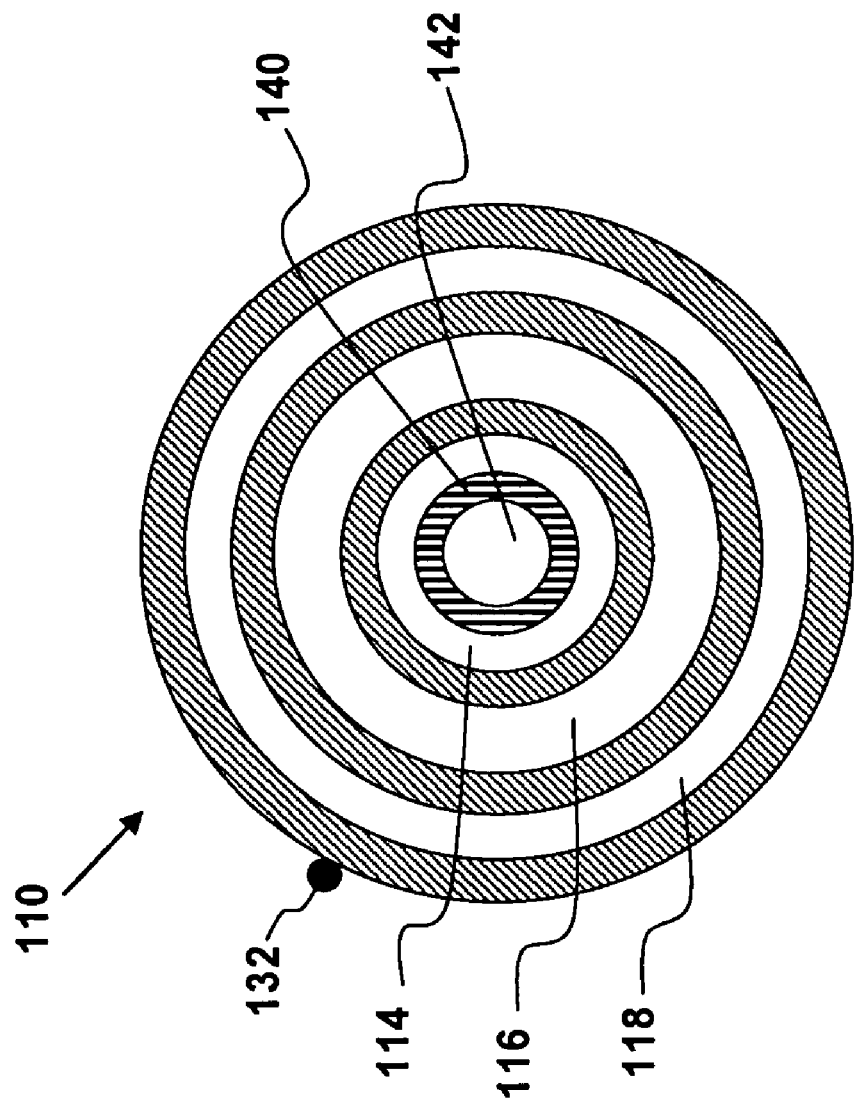
FIG. 3 is an enlarged cross-sectional view of a segment of the system of FIG. 1.

As is best seen in FIG. 3, which is an enlarged cross-sectional view of a segment of system 100, catheter 110 includes three coaxial lumens: guidewire lumen 114, fluid delivery lumen 116, and inflation lumen 118. Guidewire lumen 114, the innermost lumen, extends the length of catheter 110 to permit the catheter to be delivered to a treatment site over guidewire 140.

Fluid delivery lumen 116, the middle of the three lumens, extends from the proximal end of catheter 110 to a location adjacent to the distal end of catheter 110. Fluid delivery lumen 116 is in communication with perfusion ports 115 as well as with one or more fluid supplies. A valve or manifold system (not shown) at the proximal end of system 100 is used to deliver the appropriate fluid to fluid delivery lumen 116 at any given time. In the present embodiment, fluid delivery lumen 116 is in fluid communication with supplies of a photoinitiator, a prepolymer, and a flushing solution such as a saline solution. The term "prepolymer" is used herein to refer to any monomer, macromer, or polymer that is converted by photopolymerization in the presence of a photoinitiator to a polymer coating.

Inflation lumen 118, the outermost lumen of catheter 110, opens into proximal balloon 120 to permit inflation of the balloon. Proximal balloon 120 is disposed on catheter 110 proximal to extended tip 112. Proximal balloon 120 may be any inflatable member known in the art that is appropriate for occluding a vessel, for example a balloon made of a biocompatible material such as polyethylene, polyethylene terephthalate (PET), polyurethane, an elastomeric balloon material, or the like. To prevent formation of a polymer coating on the exterior of proximal balloon 120, the balloon may comprise a material that does not absorb or otherwise retain the photoinitiator.

Figure 2:
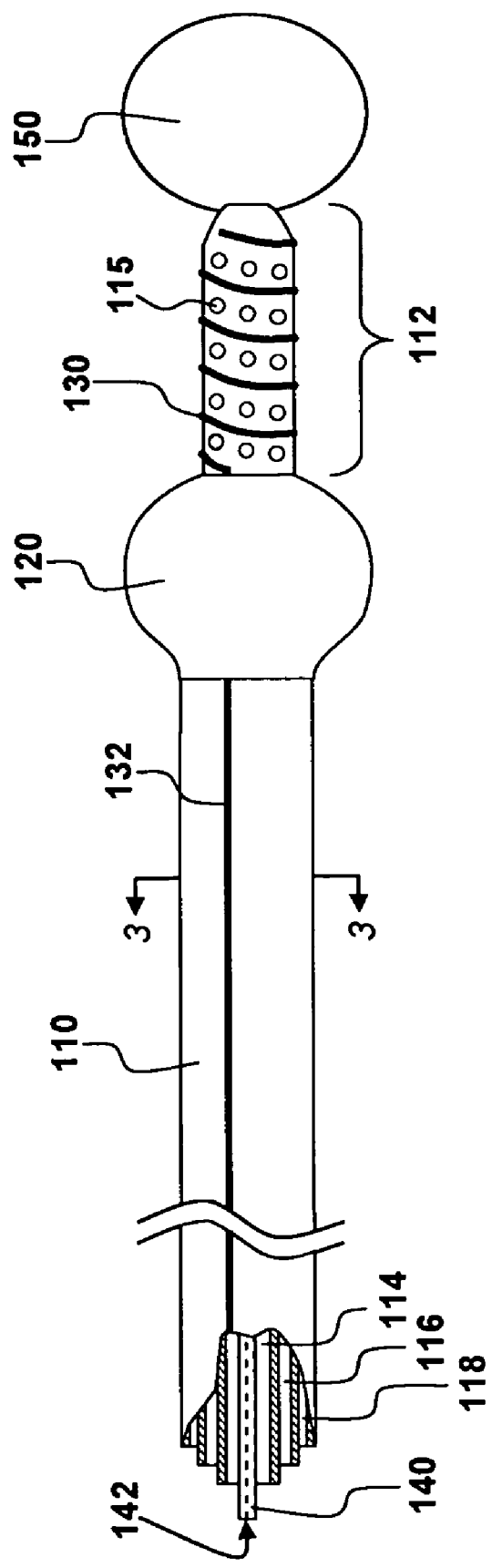
FIG. 2 is an illustration of the system of FIG. 1, showing the system as it would appear when fully delivered and ready to begin treatment.

Light emission coil 130 is disposed on extended tip 112, coaxial with the tip. In the present embodiment, light emission coil 130 is formed into a distal portion of an optical fiber. This distal portion of the fiber is abraded to diffuse light from the coil. An elongate proximal portion of the optical fiber, indicated at 132 in FIGS. 1 and 2, is substantially straight and extends under proximal balloon 120 and along the length of catheter 110, terminating at a connector arm of a luer (not shown). Alternatively, proximal portion 132 may be positioned within inflation lumen 118 rather than outside of catheter 110 as seen in FIG. 1. Light emission coil 130 is operably connected to a light source via proximal portion 132. In another embodiment, light emission coil 130 may be a section of an optical fiber that is treated in another manner to diffuse light from the fiber. In still another embodiment, light emission coil 130 may be any material capable of emitting the desired intensity of light and may be operably connected to a light source by any means of conveying light to the coil.

Perfusion ports 115 are formed into extended tip 112 in a pattern that allows the ports to be interspaced with (i.e., positioned between) individual loops of light emission coil 130. The light emission coil loops are positioned on extended tip 112 such that they do not block perfusion ports 115. One skilled in the art will appreciate that the relative positioning of perfusion ports and coil loops may be varied while still allowing adequate perfusion of a fluid through the ports. Perfusion ports 115 are in fluid communication with the photoinitiator, prepolymer, and flushing solution supplies via fluid delivery lumen 116.

Guidewire 140 may be, for example, a nitinol or stainless steel hypotube. Guidewire 140 includes an inflation lumen 142, seen in FIG. 3, to permit inflation of distal balloon 150, which is disposed on a distal portion of guidewire 140. Distal balloon 150 may be any inflatable member known in the art that is appropriate for occluding a vessel, for example a balloon comprising a biocompatible material that is the same as or different from that used to form proximal balloon 120. Guidewire 140 may include a radiopaque marker to aid in positioning the guidewire at a treatment site. Guidewire 140 is in proper position for treating the vessel when distal balloon 150 is positioned distal to the target treatment area.

Catheter 110 is delivered over guidewire 140, with guidewire 140 received within guidewire lumen 114, as can be seen in FIG. 1. Catheter 110 is extended over the guidewire until the distal end of extended tip 112 abuts the proximal end of distal balloon 150, at the point where distal balloon 150 is joined to guidewire 140. Alternatively a stop member may be positioned at the proximal end of distal balloon 150 to ensure that catheter 110 is delivered to the proper position relative to guidewire 140. The proximal end of catheter 110 may include a locking mechanism to ensure the relative positions of catheter 110 and guidewire 140 remain fixed throughout treatment of the vessel.

Distal balloon 150 remains uninflated until after catheter 110 has been delivered over and docked with guidewire 140. Both proximal balloon 120 and distal balloon 150 are then inflated, as shown in FIG. 2. In the present embodiment, proximal balloon 120 is inflated first, followed by distal balloon 150. One skilled in the art will appreciate that the order of inflation may be varied, with the distal balloon inflated before the proximal balloon or with both balloons inflated simultaneously.

Inflation of the two balloons forms an enclosed treatment space within the vessel. In the present embodiment, a photoinitiator is delivered to the treatment space via fluid delivery lumen 116 and perfusion ports 115. Distal balloon 150 acts as a fluid barrier to partially seal the treatment space while still allowing fluid to pass beyond the balloon as pressure builds up within the treatment space. Thus, distal balloon 150 creates backpressure, ensuring the treatment space becomes filled with a fluid. Distal balloon 150 is capable of partially collapsing to allow a minimal amount of fluid to exit the treatment space as needed. Proximal balloon 120 may be formed using a less malleable material than that used to form distal balloon 150 to ensure fluid exits the distal end of the treatment space.

Once the photoinitiator in contact with the vessel wall is adsorbed on (or is otherwise bound to) the tissue of the vessel wall, excess photoinitiator is flushed from the treatment space using a saline or other flushing solution. The prepolymer is then delivered to the treatment space until it fills the space. The light source operably connected to light emission coil 130 is then activated, causing the coil to deliver light to the vessel wall, thereby curing the prepolymer and forming a polymer (typically a hydrogel) coating on the wall of the vessel. The proximal 120 and distal 150 balloons may then be deflated, allowing uncured material to be washed away as the balloons contracts away from the wall of the vessel. Alternatively, uncured material may be removed prior to deflating the balloons by, for example, pulling a vacuum on fluid delivery lumen 116. The system may then be withdrawn from the vessel.

Figure 4:
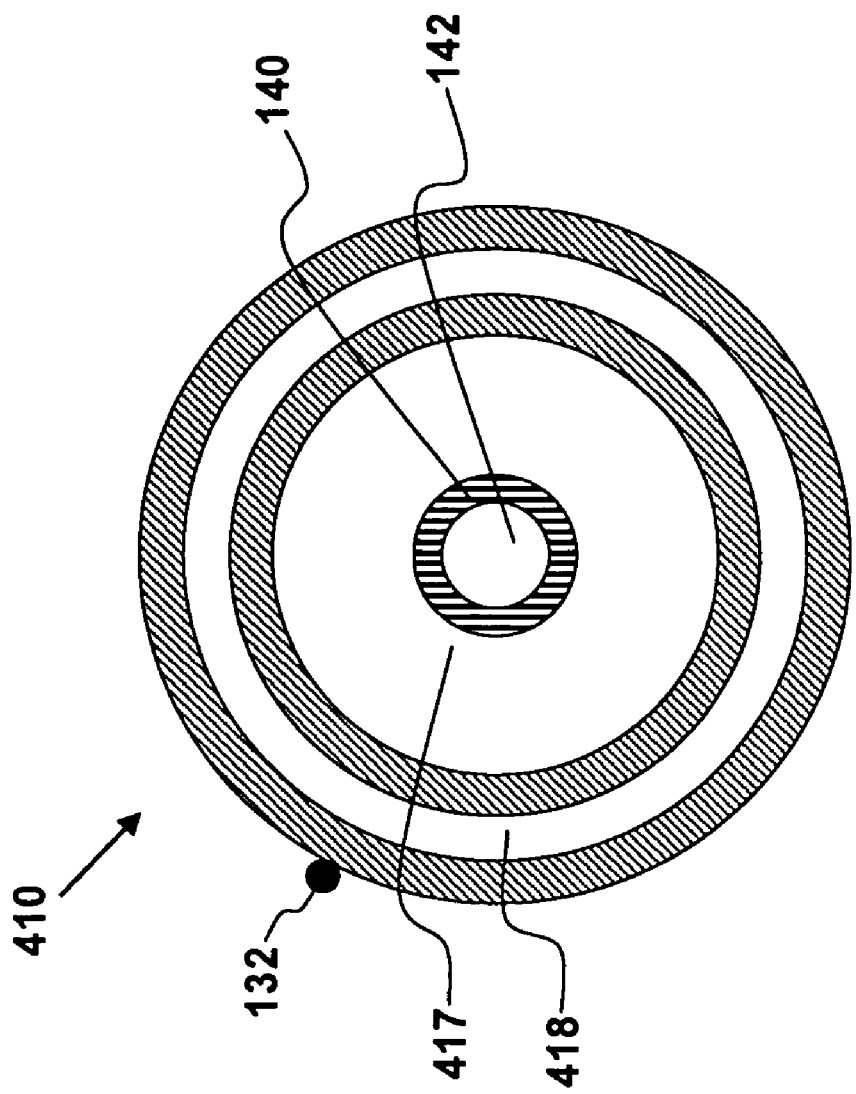
FIG. 4 is a cross-sectional view of a segment of another embodiment of a system for treating a vascular condition, in accordance with the present invention.

FIG. 4 shows a cross-sectional view of a segment of another embodiment of a system for treating a vascular condition, in accordance with the present invention. In this embodiment, catheter 410 includes two lumens, rather than three as in catheter 110, with the guidewire and fluid delivery lumens combined to form a single guidewire/fluid delivery lumen 417. This combined lumen extends the length of catheter 410. Inflation lumen 418 is external to and coaxial with guidewire/fluid delivery lumen 417.

When catheter 410 is docked with a guidewire having a distal balloon, guidewire/fluid delivery lumen 417 is sealed at its distal end by contact with the balloon/catheter bond. Alternatively, a stop member may be positioned at the proximal end of the guidewire balloon, with lumen 417 being sealed at its distal end by contact with the stop member. The combined guidewire/fluid delivery lumen may be necked down or thermally formed at its distal end to reduce the diameter of the lumen from a proximal inner diameter of about 0.030 inch to a distal inner diameter of about 0.015 inch, thereby reducing the risk of leakage occurring between the catheter and the guidewire.

Another system for treating a vascular condition comprises catheter means for occluding the vessel proximal to the treatment site, guidewire means for occluding a vessel distal to a treatment site, means for delivering a fluid to the treatment site, and means for exposing the treatment site to light along a helical path.

The catheter means for occluding a vessel distal to a treatment site may be a balloon as described above and illustrated in FIGS. 1 and 2 at 120. Alternatively, the means may include any structure that is appropriate for being carried on a catheter and occluding a vessel, for example an expandable structure that includes ribs and an outer covering, an expandable shape-memory structure having an outer covering, or an umbrella-like structure.

The guidewire means for occluding a vessel distal to a treatment site may be a balloon as described above and illustrated in FIGS. 1 and 2 at 150. Alternatively, the means may include any structure that is appropriate for being carried on a guidewire and occluding a vessel, for example an expandable structure that includes ribs and an outer covering, an expandable shape-memory structure having an outer covering, or an umbrella-like structure.

The means for delivering a fluid to the treatment site may be a fluid delivery lumen such as is described above and illustrated in FIG. 3 at 116 or a guidewire/fluid delivery lumen such as is described above and illustrated in FIG. 4 at 417. Alternatively, the means may be any lumen connecting a fluid source with a treatment area formed between the two occlusion means.

The means for exposing the treatment site to light along a helical path may be a light emission coil such as is described above and illustrated in FIGS. 1 and 2 at 130. Alternatively, the means may be any structure that performs the same function.

Figure 5:
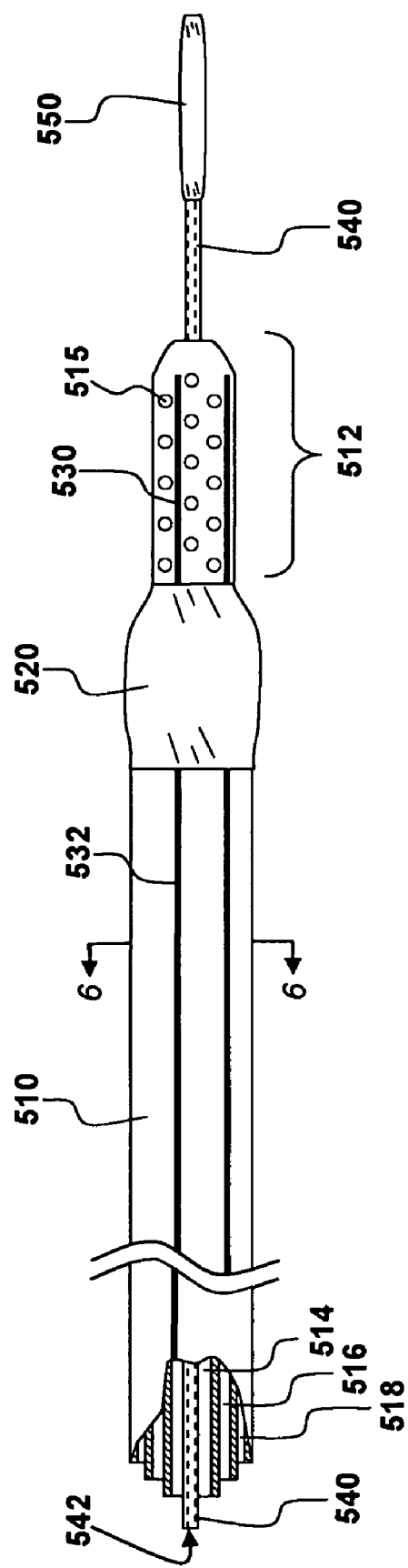
FIG. 5 is an illustration of an embodiment of another system for treating a vascular condition, in accordance with the present invention, showing the system as it would appear when partially delivered to a treatment site within a vessel.
Figure 6:
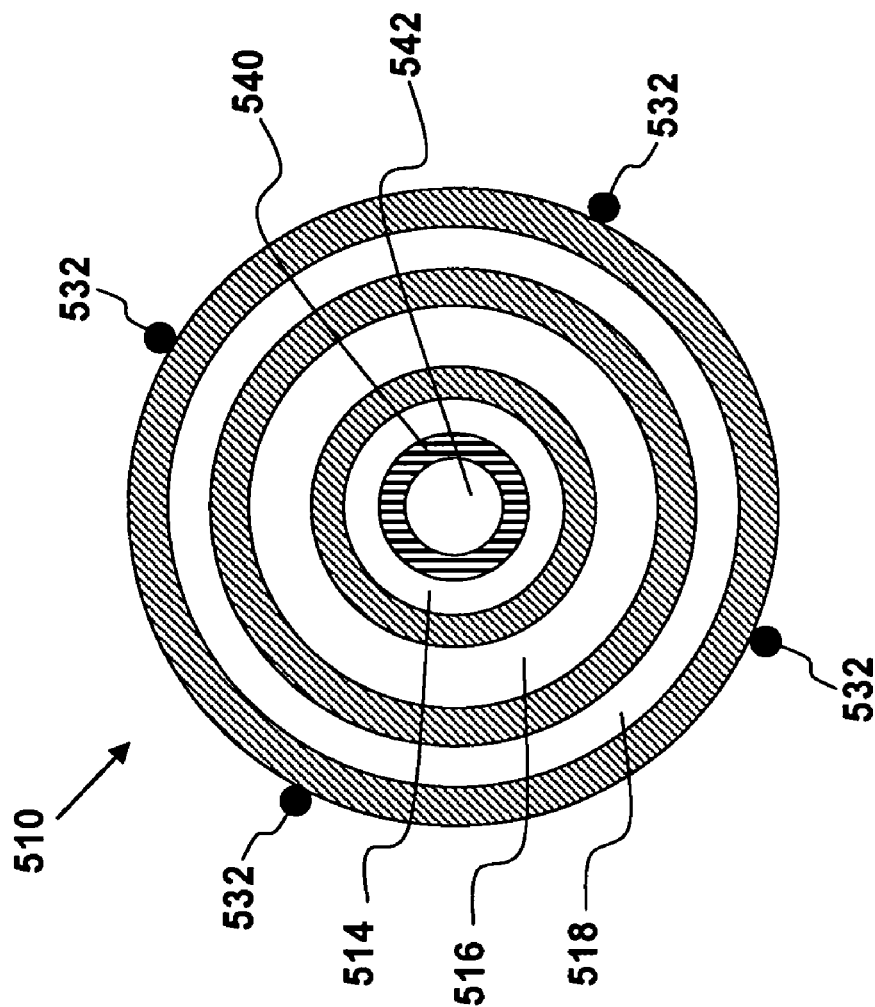
FIG. 6 is an enlarged cross-sectional view of a segment of the system of FIG. 5.

Yet another system for treating a vascular condition, in accordance with the present invention, is illustrated in FIGS. 5 and 6 at 500. System 500 comprises a catheter 510, a proximal balloon 520, multiple light emission members 530, a guidewire 540, and a distal balloon 550. Catheter 510 has an extended tip 512. A proximal portion of catheter 510 is cut away to reveal a guidewire lumen 514, a fluid delivery lumen 516, and an inflation lumen 518. Multiple perfusion ports 515 are formed in extended tip 512. Guidewire 540 includes an inflation lumen 542. The various elements of system 500 are formed using materials such as those described above with reference to system 100. As can be seen by referring to the figures, system 500 is similar in structure to system 100 with the exception that system 500 includes multiple elongate light emission members 530 in place of a light emission coil.

Light emission members 530 are substantially parallel one to another and are distributed about the circumference of extended tip 512. In the present embodiment, each light emission member 530 is formed into a distal portion of an optical fiber. This distal portion is abraded or otherwise treated to diffuse light from the optical fiber. A proximal portion of each optical fiber, indicated at 532 in FIGS. 5 and 6, extends under proximal balloon 520 and along the length of catheter 510, terminating at a connector arm of a luer (not shown). Light emission members 530 are operably connected to a light source via proximal portions 532.

System 500 includes four light emission members 530. (Two light emission members 530 are visible in FIG. 5, with two additional light emission members being hidden behind extended tip 512. All four proximal portions 532 are visible in FIG. 6.) One skilled in the art will appreciate that the number of light emission members may be varied, with more or fewer light emission members being distributed about extended tip 512. At least two light emission members are required to ensure that guidewire 540 does not cast a shadow on the vessel wall undergoing treatment.

In the illustrated embodiment, catheter 510 includes three lumens: guidewire lumen 514, fluid delivery lumen 516, and inflation lumen 518. In another embodiment, system 500 may include two lumens, with the guidewire and fluid delivery lumens combined to form a single guidewire/fluid delivery lumen. A two-lumen catheter having an inflation lumen and a combined guidewire/fluid delivery lumen is seen at 410 in FIG. 4.

In practice, a system in accordance with the present invention offers significant benefits, including, but not limited to the following. Because the distal balloon of the present invention is mounted on the guidewire, the inflation lumen for the distal balloon is contained within the guidewire rather than the catheter. This allows the catheter to have a smaller diameter, resulting in a reduced crossing profile for the system as a whole. For example, the crossing profile of a system in accordance with the present invention may be 0.060" or smaller, making it compatible with a standard 7 French guide catheter. Further, because the light is delivered by a coil or by multiple light emission members that encircle the guidewire, the guidewire may remain in place during exposure of the vessel to light without the guidewire casting a shadow on the wall of the vessel. The elimination of the additional step or withdrawing a guidewire prior to exposing the treatment site to light significantly reduces the time needed to complete the photopolymerization process, thereby reducing the risk of damage to the vessel resulting from blockage of the vessel for an extended period of time.

One skilled in the art will appreciate that, while described above in the context of forming a coating on the inner surface of a vessel, a system in accordance with the present invention may be used for other applications. For example, a coating may be formed on all or part of the inner surface of a treatment device such as a stent or graft positioned within the vessel, or on an inner surface of at least a portion of both the vessel and a treatment device. Further, the system may be used to deliver and activate materials other than photopolymerization materials, including, but not limited to, a photoactivated drug or other therapeutic agent.

Figure 7:
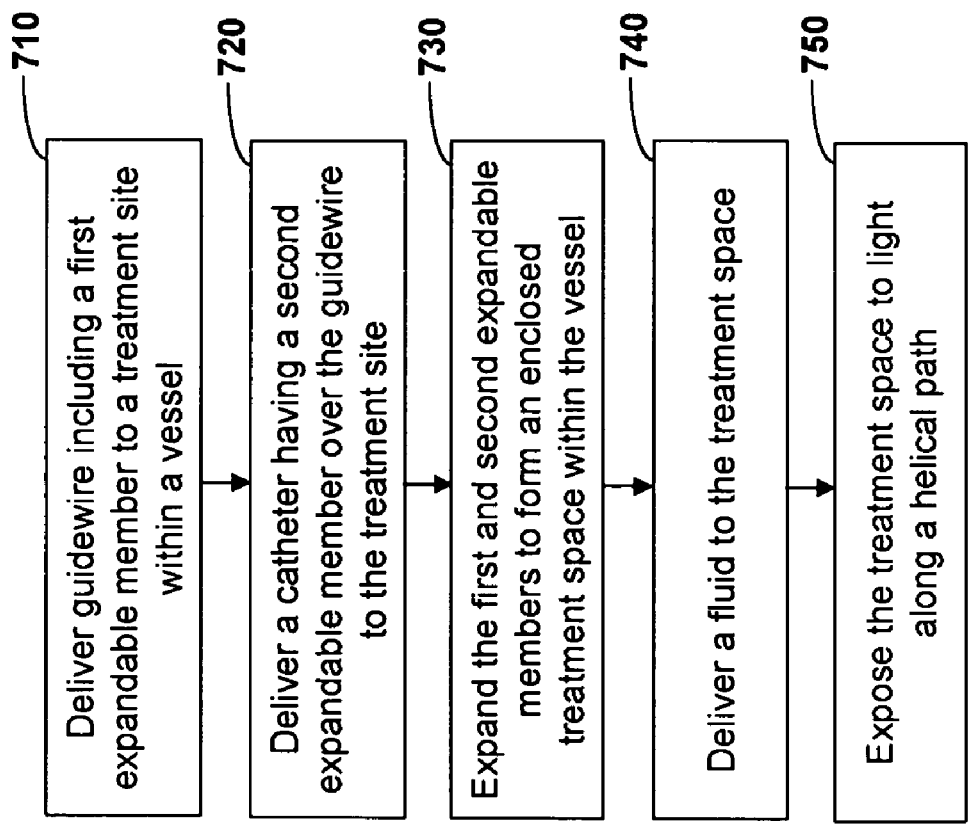
FIG. 7 is a flow diagram of one embodiment of a method of treating a vascular condition, in accordance with the present invention.

Another aspect of the present invention is a method of treating a vascular condition. FIG. 7 shows a flow diagram of one embodiment of the method in accordance with the present invention.

A guidewire including a first expandable member is delivered to a treatment site within a vessel (Block 710). For example, a guidewire having an inflatable distal balloon such as is described above and illustrated in FIGS. 1 and 2 may be delivered to a target treatment area within a blood vessel. The guidewire is properly positioned at the treatment site when the distal balloon is positioned distal to the target treatment area.

A catheter including a second expandable member is delivered over the guidewire to the treatment site (Block 720). The catheter may be as described above and illustrated in FIGS. 1 and 2, having an inflatable proximal balloon disposed on the catheter. The catheter is properly positioned at the treatment site when the distal end of the catheter abuts the proximal end of the guidewire balloon.

The first and second expandable members are expanded to form an enclosed treatment space within the vessel (Block 730). This may be accomplished as described previously, with proximal balloon 120, positioned on catheter 110, being inflated first, followed by distal balloon 150, positioned on guidewire 140, being inflated second. One skilled in the art will appreciate that the order of inflating the balloons may be varied. In addition, expandable members other than balloons may be used, with the expandable members being expanded by means other than inflation.

A fluid is delivered to the treatment space (Block 740). For example, a photoinitiator may be delivered to the treatment space, followed by a prepolymer. Excess photoinitiator is flushed from the treatment space using a saline or other flushing solution prior to delivery of the prepolymer. The photoinitiator, the flushing solution, and the prepolymer may be delivered to the treatment space via fluid delivery lumen 116 or guidewire/fluid delivery lumen 417.

The treatment space is exposed to light along a helical path (Block 750). In the present example, light is conveyed to light emission coil 130 via the proximal portion of the optical fiber used to form light emission coil 130, the proximal portion being indicated at 132 in FIGS. 1 and 2. The light forms a helical path defined by the loops of light emission coil 130. Where a system such as that illustrated at 500 in FIG. 5 is employed, the treatment space is exposed to light along multiple longitudinal paths. The longitudinal paths are substantially parallel and are spaced to ensure adequate exposure of the treatment space.

As the light is emitted by the coil or by multiple elongate light emission members, the prepolymer in contact with tissue to which photoinitiator has been bound is cured or polymerized to form a polymer (typically a hydrogel) coating on the inner wall of the vessel. Once the polymer coating has been formed, the expandable members may be returned to their unexpanded configurations, and the catheter and guidewire may be withdrawn from the vessel, either individually or together.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A method of treating a vascular condition, the method comprising:
    delivering a guidewire to a treatment site within a vessel, the guidewire including a first expandable member;
    delivering a catheter over the guidewire to the treatment site, the catheter including a second expandable member and an extended tip, the extended tip including a plurality of perfusion ports distributed about a circumference of the extended tip; a light emission coil disposed on an outside surface of the extended tip, the light emission coil coaxial with the extended tip, wherein the perfusion ports are spaced between loops of the light emission coil;
    expanding the first and second expandable members to form an enclosed treatment space within the vessel;
    delivering a fluid to the treatment space; and
    exposing the treatment space to light via the light emission coil.

2. The method of claim 1 wherein expanding the first and second expandable members to form an enclosed treatment space within the vessel comprises:
    first expanding the second expandable member; and
    then expanding the first expandable member.

3. The method of claim 1 further comprising:
    flushing the treatment space with a flushing solution after delivering the fluid to the treatment space.

4. The method of claim 3 further comprising:
    delivering a second fluid to the treatment space after flushing the treatment space with a flushing solution.

5. The method of claim 4 wherein the second fluid is a prepolymer.

6. The method of claim 5 wherein exposing the treatment space to light comprises photopolymerizing at least a portion of the prepolymer to form a polymer coating on the inner wall of the vessel.

7. The method of claim 1 wherein the treatment space is exposed to light along a helical path.

8. The method of claim 1 wherein the treatment space is exposed to light along multiple longitudinal paths.

* * * * *